(12) United States Patent
Elfström et al.

(10) Patent No.: US 7,632,259 B2
(45) Date of Patent: Dec. 15, 2009

(54) ABSORBENT ARTICLE

(75) Inventors: Anna-Karin Elfström, Torslanda (SE);
Cécile Sandin, Mölndal (SE); Kent Hermansson, Vastra Frölunda (SE);
Kenneth Strannemalm, Floda (SE);
Carina Mare, Västra Frölunda (SE);
Lennart Nilsson, Skärhamn (SE)

(73) Assignee: SCA Hygiene Products AB, Gothenburg (SE)

( * ) Notice: Subject to any disclaimer, the term of this patent is extended or adjusted under 35 U.S.C. 154(b) by 443 days.

(21) Appl. No.: 10/283,312

(22) Filed: Oct. 30, 2002

(65) Prior Publication Data

US 2003/0093055 A1    May 15, 2003

Related U.S. Application Data

(60) Provisional application No. 60/330,777, filed on Oct. 31, 2001.

(51) Int. Cl.
*A61F 13/15* (2006.01)
*A61F 13/20* (2006.01)

(52) U.S. Cl. .......................... 604/385.27; 604/385.101

(58) Field of Classification Search .......... 604/385.101, 604/378, 380, 385.01, 387, 385.25–385.3; 2/400, 401, 406
See application file for complete search history.

(56) References Cited

U.S. PATENT DOCUMENTS

| | | | |
|---|---|---|---|
| 4,695,278 A | | 9/1987 | Lawson |
| 4,738,677 A | | 4/1988 | Foreman |
| 5,064,489 A | | 11/1991 | Ujimoto et al. |
| 5,415,649 A | * | 5/1995 | Watanabe et al. ...... 604/385.29 |
| 5,554,145 A | * | 9/1996 | Roe et al. ................ 604/385.3 |
| 5,634,917 A | * | 6/1997 | Fujioka et al. ......... 604/385.29 |
| 5,735,839 A | | 4/1998 | Kawaguchi et al. |

(Continued)

FOREIGN PATENT DOCUMENTS

EP    0 761 193 A2    3/1997

(Continued)

OTHER PUBLICATIONS

An English Translation of Notice of Reasons for Rejection in JP 2003-539584 dated Oct. 7, 2008.

(Continued)

*Primary Examiner*—Michele Kidwell
(74) *Attorney, Agent, or Firm*—Buchanan Ingersoll & Rooney PC

(57) ABSTRACT

An absorption article such as a pant diaper, having a liquid-permeable topsheet, a liquid-impermeable backsheet and an absorption body positioned therebetween, the article having a front end portion, a rear end portion, and a crotch portion lying therebetween, the rear end portion and the adjacent part of the crotch portion having a transverse elastic system, a rear leg elastic system which runs between the two longitudinal side edges of the article along the leg cutout of the article in the rear part of the crotch portion and crosses the crotch portion essentially parallel to the transverse center line of the article. The article has, on each side of the absorption body, a pocket for temporary storage of liquid, the extent of the pocket being limited by the longitudinal side edge of the absorption body, the transverse elastic system and the rear leg elastic system.

21 Claims, 3 Drawing Sheets

U.S. PATENT DOCUMENTS

| | | | |
|---|---|---|---|
| 5,910,137 A * | 6/1999 | Clark et al. ................. 604/387 |
| 5,993,433 A | 11/1999 | St. Louis et al. |
| 6,098,203 A | 8/2000 | Rajala et al. |
| 6,179,820 B1 | 1/2001 | Fernfors |
| 6,240,569 B1 * | 6/2001 | Van Gompel et al. .......... 2/400 |
| 6,260,211 B1 * | 7/2001 | Rajala et al. ................... 2/401 |
| 6,367,089 B2 * | 4/2002 | Van Gompel et al. .......... 2/406 |
| 2002/0007172 A1 * | 1/2002 | Takei et al. ............ 604/385.27 |
| 2003/0088223 A1 * | 5/2003 | Vogt et al. ............. 604/385.01 |

FOREIGN PATENT DOCUMENTS

| | | |
|---|---|---|
| EP | 0 761 194 A2 | 3/1997 |
| EP | 0 264 238 B2 | 12/1999 |
| GB | 2 188 532 A | 10/1987 |
| GB | 2262873 A * | 7/1993 |
| JP | 04-242643 | 8/1992 |
| JP | 04-242645 | 8/1992 |
| JP | 08-024291 | 1/1996 |
| JP | 08-112309 | 5/1996 |
| JP | 11-151265 | 6/1999 |
| JP | 11-188062 | 7/1999 |
| JP | 11-511664 T | 10/1999 |
| JP | 2001-087314 | 4/2001 |
| JP | 2001-252302 | 9/2001 |
| JP | 2001-258931 | 9/2001 |
| WO | 92/07535 | 5/1992 |
| WO | 96/11657 | 4/1996 |
| WO | 99/16398 | 4/1999 |
| WO | 99/18904 | 4/1999 |
| WO | 99/25296 * | 5/1999 |

OTHER PUBLICATIONS

An English Translation of the Notice of Grounds for Refusal in KR 10-2004-7006426 dated Mar. 30, 2009.

* cited by examiner

ABSORBENT ARTICLE

CROSS-REFERENCE TO RELATED APPLICATION

This application claims priority to U.S. provisional Application Ser. No. 60/330,777, filed Oct. 31, 2001, the text of which is hereby incorporated by reference and relied upon for all purposes.

FIELD OF THE INVENTION

An absorbent article such as an incontinence device of the pant type, or a pant diaper, comprising a liquid-permeable topsheet, a liquid-impermeable backsheet and an absorption body positioned therebetween, the absorption body having an elongate shape with two longitudinal side edges and two transverse side edges, the article having two longitudinal side edges, a longitudinal center line, a transverse center line, a front end portion which is intended during normal use to lie against or in proximity to the abdomen of the wearer, a rear end portion which is intended during normal use to lie against or in proximity to the bottom of the back of the wearer, and a crotch portion lying therebetween, the rear end portion and the adjacent part of the crotch portion having a transverse elastic system, a rear leg elastic system which runs between the two longitudinal side edges of the article along the leg cutout of the article in the rear part of the crotch portion and crosses the crotch portion essentially parallel to the transverse center line of the article.

BACKGROUND OF THE INVENTION

There are a number of different types of incontinence, one of them being what is known as stress incontinence. Stress incontinence means that urine leakage can occur when stress takes place, for example when the sufferer coughs, sneezes, laughs, jumps or carries heavy items, i.e. when certain muscles are stretched. There can be many causes of stress incontinence, and a great deal of research is being undertaken within the area. One of the causes of stress incontinence can be that the muscles which are meant to hold the urethra in place have become weakened; in principle it could be said that the urethra is poorly fastened or poorly fixed in the body. This means that the urethra can slide out of position especially when it is subjected to an increase in pressure in the abdominal cavity, for example when a person laughs. The bladder is situated in the abdominal cavity, and if it is subjected to increased pressure, the muscles are usually capable of resisting, but this is not the case in stress incontinence.

The result of such stress incontinence as just described leading to leakage of urine can feel relatively violent at the moment it occurs, i.e. relatively large volumes of urine may be passed, even as much as 50 cl in the course of a few seconds. This of course places great demands on incontinence devices and other absorbent articles. One way of solving the problem of stress incontinence leakage is to have what are known as raised leakage barriers (also referred to as standing gathers) on the absorbent article.

The leakage barriers are in most cases positioned inside the leg elastic and in most cases consist of a liquid-impermeable material, for example non-woven fabric, but can also be made of liquid-permeable material. The leakage barriers usually extend in the longitudinal direction with the absorption body and are formed by a web, one longitudinal edge of which is attached to the absorbent article and the other, free end of which is intended to lie against the wearer. The free edge is elastically gathered by means of an elastic thread which is folded into the edge of the web. Examples of absorbent articles with leakage barriers (or what are also referred to as liquid barriers) are described in, for example, WO-A1-9207533, U.S. Pat. No. 4,695,278, U.S. Pat. No. 5,064,489, SE-T3-0264238 and GB-A-2188532.

The problem is of course even greater in the case of absorbent articles without these raised leakage barriers. In these articles, there is in most cases only the leg elastic as a barrier or protection against leakage during these temporary urine discharges. Another way of solving this nature of problem for absorbent articles without raised leakage barriers is to bring about a sufficiently good fit so that no leakage can occur.

A common approach is to attempt to have as rapid admission as possible through the liquid-permeable topsheet to the underlying absorption body. There are, however, physical limitations to how rapidly the admission can take place.

U.S. Pat. No. 5,634,917, Fujioka, describes an absorbent article with a number of different possible leg elastic combinations. In one specific embodiment, a first elastic part runs along the leg cutout and crosses the crotch portion horizontally. In the same way, a second elastic part runs along the opposite leg cutout and crosses the crotch portion horizontally. The first and the second elastic parts describe a "U" and an inverted "U" in a central part of the crotch portion. The first and the second elastic parts are also to be separated from one another by a distance "D" in a central part of the crotch portion (see FIG. 7). Although Fujioka touches on a major problem, the document leaves a number of loose ends with scope for improvement.

WO 96/11657, Kawaguchi, describes an absorbent article of the "shorts" type. The document states that it comprises two inventions which together will solve the problems associated with the article sliding down from the wearer on account of the weight of the motion so that leakage occurs. The invention is also said to solve the problem of good fit and to prevent the article swelling. The solution for this is to have a number of elastic threads in or in proximity to the wetting zone, i.e. in the front part of the article, in combination with having a number of elastic threads in "the body surrounding portion", i.e. in the waist, in such a manner that the distance between them becomes smaller the closer they come to the waist opening.

Another problem encountered with this type of article is leakage on account of the absorption body being subjected to pressure, for example when the wearer sits or lies down. The urine can then be pressed back out of the absorption body, especially if the urine evacuation has taken place recently and the urine has not had time to spread in the absorption body so that the capacity of the whole absorption body has been utilized. It can also happen that the absorption body is subjected to pressure by the wearer at the moment when urine evacuation takes place. This means that the absorption body can have an instantaneously somewhat deteriorated absorption capacity, which requires some form of compensation.

It is therefore not always sufficient to have a good fit. The documents just mentioned indicate different ways of attempting to solve the problems associated with the fit in order to prevent leakage by creating various elastic patterns. However, a great many unsolved problems remain, and the elastic picture is in no way complete, a good fit does not necessarily mean that a heavy instantaneous urine evacuation can be absorbed by the absorption body, especially if it is subjected to pressure or if it will be subjected to pressure directly after urine evacuation. The documents do not go into the problem of heavy instantaneous urine evacuation which what is known as stress incontinence can give rise to. The optimum solution to the problem should therefore not be only to provide protection for these instantaneous urine evacuations but also to ensure that a good fit is maintained or even improved. It is also to be relatively simple to carry out industrial production and also preferably to give the wearer added value in addition to the solution itself to the problem.

SUMMARY OF THE INVENTION

By means of the present invention, an absorbent article of the type referred to in the introduction has been produced, which article essentially eliminates the problems associated with previously known such articles. An article made according to the invention is characterized mainly in that the article has, on each side of the absorption body, a pocket for temporary storage of liquid, the extent of the pocket being limited by the longitudinal side edge of the absorption body, the transverse elastic system and the rear leg elastic system.

The rear elastic system pulls in the outermost part of the absorption body so that the article is thin and flexible. This means that the article is not visible under clothing when it is in use. This also improves the fit and means that the article lies like an item of underwear. The transverse elastic system creates a pocket on each side of the absorption body. The transverse elastic system is designed so as to conduct and retain the urine which is instantaneously discharged in a great quantity into the pockets. This is brought about by virtue of the elastic delimiting the extent of the pockets so that only the absorption body can take up the liquid. This can be effected by virtue of, inter alia, the fact that the transverse elastic system crosses at least a part of the rear leg elastic system in the rear part of the crotch portion at the leg cutout of the article.

According to one embodiment, the distance A (as will be described below in connection with FIG. 4 shown in the drawings) between the rear leg elastic system and the transverse elastic system, measured along the longitudinal center line of the article, is used for the design of the pockets. The distance is preferably 29-81 mm, more preferably 34-71 mm, and most preferably 39-61 mm in order for fit and function to be optimized. The transverse elastic system can consist of a number of different systems, for example as shown in FIG. 1, where the transverse elastic system comprises three different elastic systems. It is also within the scope of the invention for the transverse elastic system to be a large number of threads or an individual thread, one or more elastic band(s), an elastic film, a separate elastic part of the like.

In order for the article to be comfortable to use but still afford a tight fit, it is preferable that the transverse elastic system can be stretched to 1.8 times its unstretched length. The unstretched length means when the elastic is in the contracted state, that is to say the gathered state.

According to one embodiment, the transverse elastic system consists of a number of essentially parallel elastic threads with a given mutual spacing. Elastic threads have been found to be advantageous to work with in terms of process engineering, also providing comfort and a good fit. Given spacing means that the threads are not to lie at an irregular spacing from one another. The threads can have different regions with different spacings, but within each individual region the threads have the same spacing from one another. All the threads can also have the same spacing from one another.

In order for it to be possible for the transverse elastic system to be flexible but also to constitute a part of the liquid-receiving space, it is preferable that the elastic can instantaneously be extended, that is to say stretched, when large quantities of liquid are passed. It is preferable, therefore, that the elastic not be as tight-fitting in and around the crotch portion as around the waist because it has a different function there, namely to hold the article in place. The transverse elastic system therefore advantageously consists of at least a second rear elastic system and if appropriate a third rear elastic system also. The second and third elastic systems can have different elasticity, and this may be achieved by virtue of either weaker elastic or, for example, a smaller number of elastic threads running in the elastic area. It can also be achieved by virtue of the spacing between the elastic threads of the second rear elastic system being smaller than the spacing between the threads in the third rear elastic system.

As it is important that the instantaneously discharged urine is dealt with by the absorption body, it is preferably not only readily accessible but also the right sort of absorption layer which can distribute the liquid within the absorption layer which is available. Absorption bodies in various layers are usually constructed with a liquid-spreading layer next to the liquid-permeable topsheet. The liquid-spreading layer is in most cases followed by a layer with a certain storage capacity which can nevertheless additionally spread the liquid horizontally but also vertically to adjacent storage layers.

As the absorption body consists of at least a first and a second absorption layer, the first absorption layer being longer in the longitudinal direction than the second absorption layer, and the second absorption layer being at least 16 cm long in the longitudinal direction, the second absorption layer can be exposed to the liquid in the pockets which are formed on each side of the absorption body in the rear part of the crotch portion and in the rear end portion. In one embodiment, the article also comprises a front leg elastic system, and the distance between the front elastic system and the rear leg elastic system in the crotch portion is at least 16 cm.

BRIEF DESCRIPTION OF THE DRAWINGS

The invention will be described in greater detail below with reference to the figures shown in the accompanying drawings.

DETAILED DESCRIPTION OF THE INVENTION

The invention relates to an absorbent article such as a pant diaper, an incontinence device of the pant type, or the like. It is principally an incontinence device which is described below.

Figure 1:
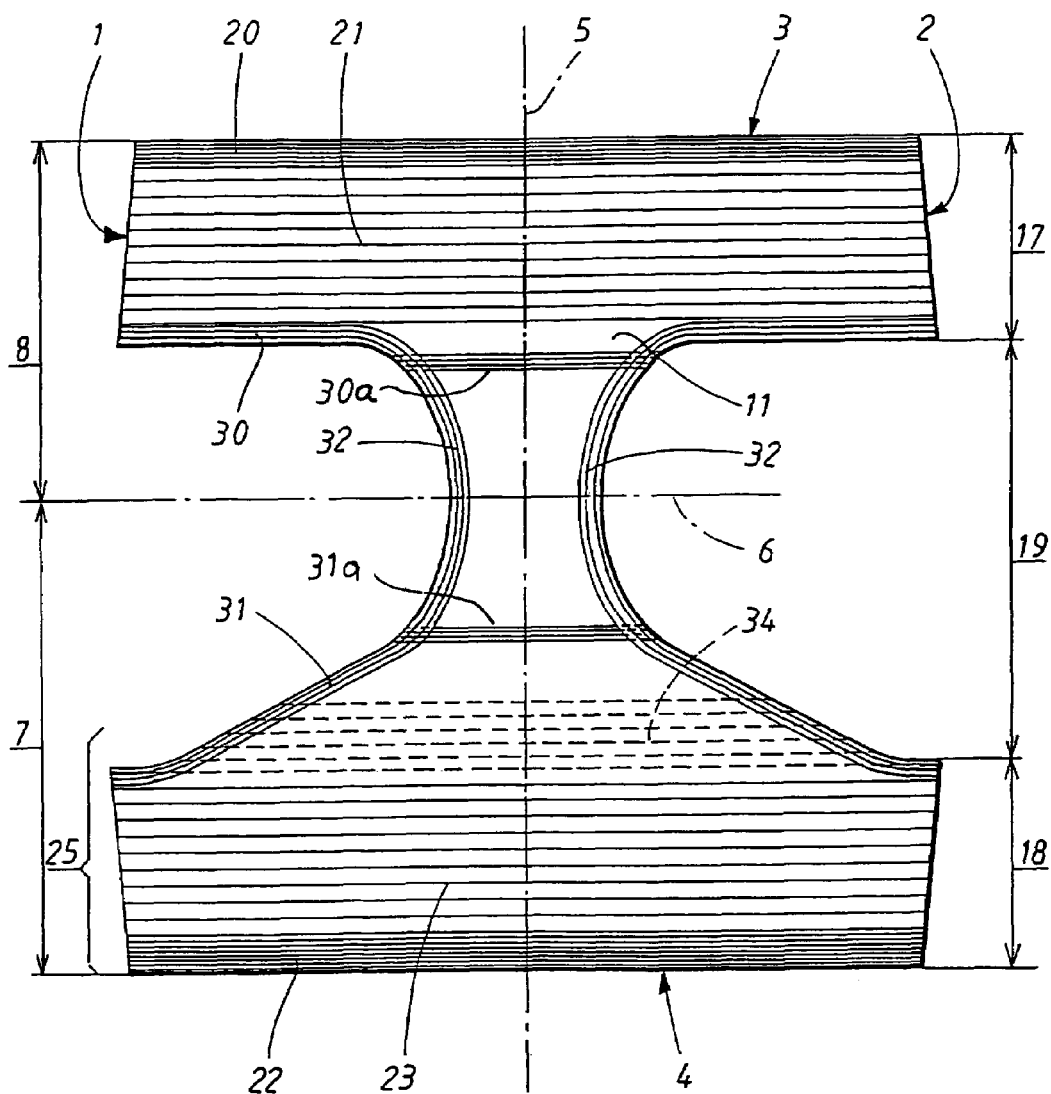
FIG. 1 shows an incontinence device of the pant type in the extended state in a view towards the liquid-impermeable side.

The article, seen from the outside in its folded-out state in FIG. 1, has two longitudinal side edges 1, 2, a front transverse side edge 3, a rear transverse side edge 4, a longitudinal center line 5, and a transverse center line 6. A rear part 7 extends between the transverse center line 6 of the article and the rear transverse side edge 4 of the article, and a front part 8 extends between the transverse center line 6 of the article and the front transverse side edge 3 of the article.

A liquid-impermeable backsheet 11 is also visible in the figure. The liquid-impermeable backsheet 11 can consist of or comprise a liquid-impermeable plastic film, a non-woven layer, a non-woven laminate or the like. The backsheet 11 can have been coated with liquid-blocking material, or a flexible material layer which has the capacity to resist liquid penetration. It is in general an advantage if the liquid-impermeable backsheet 11 is breathable, that is to say allows water vapour to pass through the sheet.

The article has a front end portion 17 located in the front part 8 of the article, a rear end portion 18 located in the rear part 7 of the article, and a crotch portion 19 lying therebetween. The front end portion 17 is intended during normal use to lie against or in proximity to the abdomen of the wearer. The rear end portion 18 is intended during normal use to lie against or in proximity to the bottom of the back of the wearer.

The front end portion 17 has a first front elastic system 20 and a second front elastic system 21. The first front elastic system 20 runs essentially along the front transverse side edge 3 of the article. The second front elastic system 21 runs essentially parallel to the transverse center line 6 of the article between the crotch portion 19 and the first front elastic system 20.

The rear end portion 18 has a first rear elastic system 22 and a second rear elastic system 23. The first rear elastic system 22 runs essentially along the rear transverse side edge 4 of the article. The second rear elastic system 23 runs essentially parallel to the transverse center line 6 of the article between the crotch portion 19 and the first rear elastic system 22.

The first and second elastic systems 20, 21, 22, 23 consist of a number of essentially parallel elastic threads which, as mentioned above, run essentially parallel to the transverse center line 6 of the article. When the article is used, the longitudinal side edges 1, 2 of the front and rear end portions 17, 18 are joined together so that the article is in the form of pants. Broadly speaking, the first and second elastic systems 20, 21, 22, 23 therefore run continuously around the waist of the wearer during use, with the exception of the interruptions at the joins.

The article also has a first front leg elastic system 30 and a first rear leg elastic system 31, and also a second leg elastic system 32.

According to FIG. 1, the first front leg elastic system 30 consists of a number of elastic threads. The elastic threads run from the longitudinal edge 1 of the front end portion 17 along the almost U-shaped leg cutout, which is intended to surround the leg of the wearer during use, until the leg cutout turns off to run in the longitudinal direction with the longitudinal center line 5 of the article. At this point, the threads of the first front leg elastic system 30 run from the first longitudinal side edge 1 of the article in a direction essentially parallel to the transverse center line 6 of the article to the opposite point on the second longitudinal side edge 2 of the article; thereby defining a transverse part 30a of the first front leg elastic system 31. The elastic threads then follow the U-shaped leg cutout in a corresponding manner to the second longitudinal side edge 2 of the front end portion 17.

According to FIG. 1, the first rear leg elastic system 31 consists of a number of elastic threads. The elastic threads run from the longitudinal edge 1 of the rear end portion 18 along the almost U-shaped leg cutout, which is intended to surround the leg of the wearer during use, until the leg cutout turns off to run in the longitudinal direction with the longitudinal center line 5 of the article. At this point, the threads of the first rear leg elastic system 31 run from the first longitudinal side edge 1 of the article in a direction essentially parallel to the transverse center line 6 of the article to the opposite point on the second longitudinal side edge 2 of the article; thereby defining a transverse part 31a of the first rear leg elastic system 31. The elastic threads then follow the U-shaped leg cutout in a corresponding manner to the second longitudinal side edge 2 of the rear end portion 18. The distance between the transverse part 30a of the first front leg elastic system and the transverse part 31a of the first rear leg elastic system defines the distance between the front elastic leg system and the rear leg elastic system in the crotch portion of the absorbent article, and is preferably at least approximately 16 cm.

According to FIG. 1, the second leg elastic system 32 consists of a number of elastic threads which run along the leg cutout, i.e. that part of the longitudinal side edges 1, 2 of the article at the leg cutout in the crotch portion 19 where no first leg elastic system 30, 31 runs. Said elastic 32 has a slightly concave shape in relation to the longitudinal center line 5 of the article so as to achieve an optimum fit in relation to the legs of the wearer. The second leg elastic system 32 is applied together with the absorption core 12 (see FIGS. 2 and 3) as a "unit".

The article also has an additional third rear elastic system 34, running essentially parallel to the transverse center line 6 of the article and located between the transverse part of the rear leg elastic system 31, which is essentially parallel to the transverse center line 6, and the second rear elastic system 23 so that it crosses at least a part of the first rear leg elastic system 31 along the longitudinal side edges 1, 2 of the crotch portion 19. The third rear elastic system 34 forms, together with the absorption body 12 and the rear leg elastic 31, a liquid-receiving pocket 35, 36 on each side of the absorption body 12, the extent of which is limited by the longitudinal side edge 13, 14 of the absorption body 12, the third elastic system 34 and the first rear leg elastic system 31. This means that there is a temporary storage space for the liquid when the wearer has heavier evacuations of urine in the event of, for example, a sneeze or the like.

Figure 2:
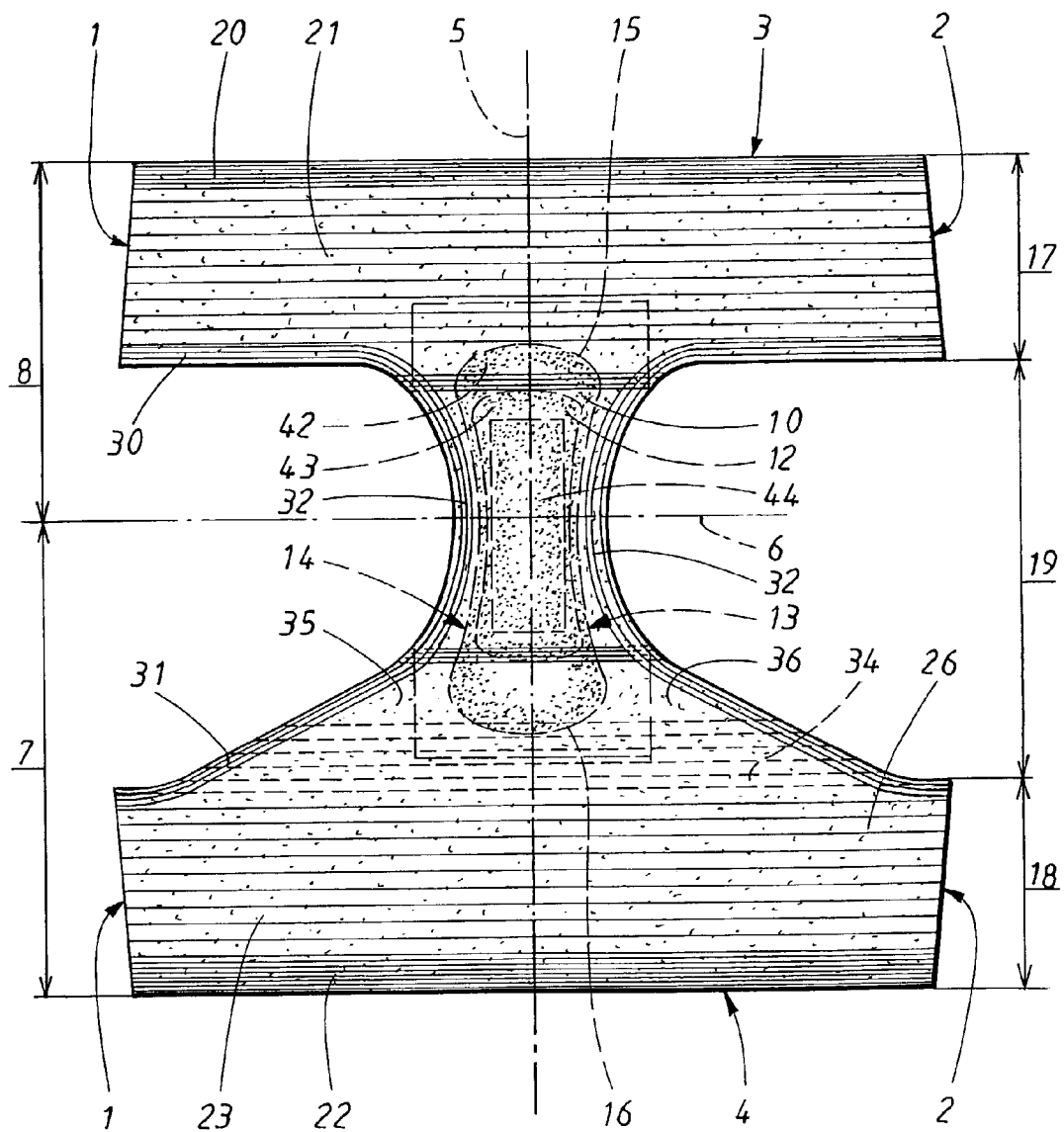
FIG. 2 shows an incontinence device like in FIG. 1, in a view towards the liquid-permeable side.

The first, second and third elastic systems are located between the liquid-impermeable backsheet 11 and the inner topsheet 26 shown in FIG. 2.

In FIG. 2, the article is seen from the inside, i.e. the side which is intended to face the genitals of the wearer during use. The article in FIG. 2 therefore has two longitudinal side edges 1, 2 and two transverse side edges 3, 4, a longitudinal center line 5 and a transverse center line 6. A rear part 7 extends between the transverse center line 6 of the article and one transverse side edge 4 of the article, and a front part 8 extends between the transverse center line 6 of the article and the other transverse side edge 3 of the article.

As mentioned above, the article has a front end portion 17 located in the front part 8 of the article, a rear end portion 18 located in the rear part 7 of the article, and a crotch portion 19 lying therebetween. The front end portion 17 is intended during normal use to lie against or in proximity to the abdomen of the wearer. The rear end portion 18 is intended during normal use to lie against or in proximity to the bottom of the back of the wearer.

Figure 3A:
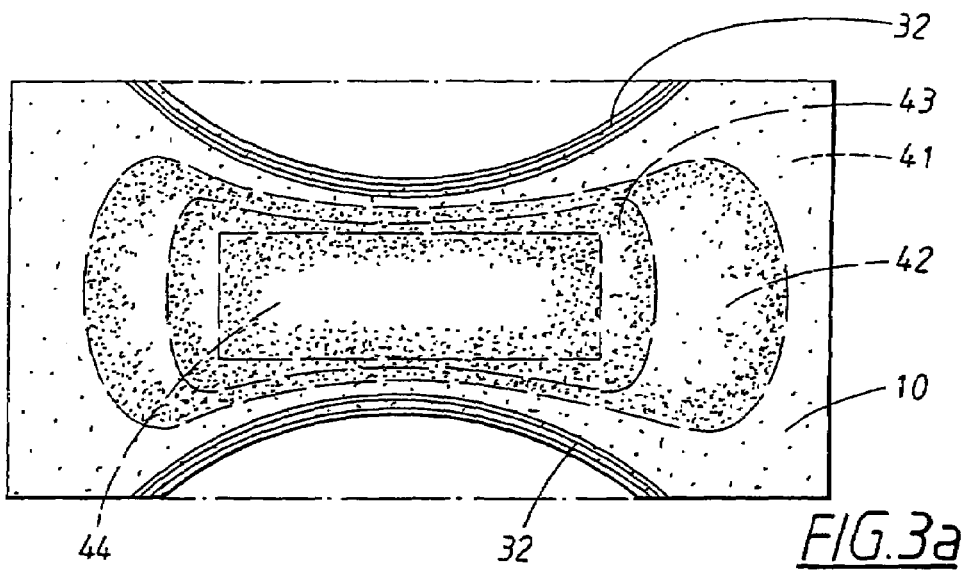
FIGS. 3*a* and 3*b* show leg elastic and the construction of the absorption body.
Figure 3B:
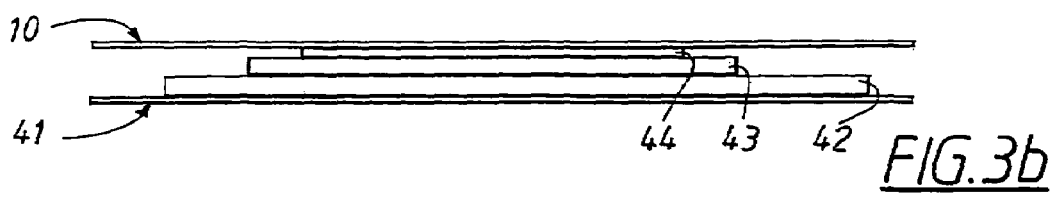

The article in FIG. 2 has an inner liquid-impermeable topsheet 26 which is preferably breathable, and an absorption body 12, which has an elongate shape with two longitudinal side edges 13, 14 and two transverse side edges 15, 16, with a liquid-permeable topsheet 10 (also described in FIGS. 3a and 3b). The absorption body also has a first and a second absorption layer 42, 43, the longitudinal side edges 13, 14 of the first absorption layer being equivalent to the longitudinal side edges 13, 14 of the absorption body. The first absorption layer 42 is preferably longer in the longitudinal direction than the second absorption layer 43, the second layer 43 being at least 16 cm long in the longitudinal direction. The absorption body 12 also comprises a liquid-receiving layer 44 (also referred to as an acquisition layer) located between the liquid-permeable topsheet 10 and the second absorption layer 43. The absorption body 12 also comprises a backsheet 41 which can be liquid-impermeable but does not have to be as the article has a liquid-impermeable backsheet 11 and a liquid-impermeable inner topsheet 26. In some embodiments, the backsheet 41 of the absorption body 12 can be liquid-impermeable, and the backsheet 11 of the article and the inner topsheet 26 of the article not liquid-impermeable. The sheets 11, 26 and 41 are nevertheless preferably breathable.

A non-woven material is usually used as the liquid-permeable topsheet 11 in absorbent articles, such as diapers and incontinence devices. One material which is used is, for example, non-woven material made of polypropylene fibres. Other materials may be mixtures of polypropylene fibres and polyethylene fibres. Materials which are hydrophobic are usually treated with an agent which makes them more hydrophilic. Use can obviously be made of materials which are hydrophilic. Perforated plastic material and various sorts of laminate are of course also included within the scope of the invention.

FIG. 2 also shows a front end portion 17 located in the front part 8 of the article, a rear end portion 18 located in the rear part 7 of the article, and a crotch portion 19 lying therebetween. The front end portion 17 is intended during normal use to lie against or in proximity to the abdomen of the wearer. The rear end portion 18 is intended during normal use to lie against or in proximity to the bottom of the back of the wearer.

The front end portion 17 has a first front elastic system 20 and a second front elastic system 21. The first front elastic system 20 runs essentially along the front transverse side edge 3 of the article. The second front elastic system 21 runs essentially parallel to the transverse center line 6 of the article between the crotch portion 19 and the first front elastic system 20.

The rear end portion 18 has a first rear elastic system 22 and a second rear elastic system 23. The first rear elastic system 22 runs essentially along the rear transverse side edge 4 of the article. The second rear elastic system 23 runs essentially parallel to the transverse center line 6 of the article between the crotch portion 19 and the first rear elastic system 22.

FIG. 2 also shows the first front and rear leg elastic systems 30, 31 and the second leg elastic system 32.

The second leg elastic system 32 runs in essentially the same direction as the longitudinal center line 5 of the article between the front and the rear end portions 17, 18. Said elastic 32 has a slightly concave shape in relation to the longitudinal center line 5 so as to achieve an optimum fit in relation to the legs of the wearer. The second leg elastic system 32 is applied together with the absorption body 12 (see FIGS. 3a and 3b) as a "unit".

FIG. 2 also shows a third rear elastic system 34, running essentially parallel to the transverse center line 6 of the article. The third rear elastic system 34, the longitudinal side edges 13, 14 of the absorption body and the first rear leg elastic system form, on each side of the absorption body 12, a pocket 35, 36 for temporary storage of liquid. This means that when the wearer has heavier evacuations of urine in the event of, for example, a sneeze or the like, the liquid can be stored temporarily in the pockets 35, 36 so that the absorption body has time to absorb all the liquid.

In FIG. 2, the second front elastic system 21 is tangent to one transverse side edge 15 of the absorption body 12 in the front end portion 17 of the article but could just as well go down past the transverse side edge 15.

FIGS. 3a and 3b show how the absorption body 12 and the second leg elastic system 32 are constructed. The absorption body 12 lies on an absorption body backsheet 41 made of an essentially liquid-impermeable, but preferably breathable, material. The absorption body backsheet 41 is intended to face away from the skin of the wearer during use of the article.

A first and a second absorption layer 42, 43 are attached to the absorption body backsheet 41. Between the second absorption layer 43 and the liquid-permeable topsheet 10 is a liquid-receiving layer 44, the primary function of which is to spread the liquid rapidly so that the first and the second absorption layers 42, 43 can absorb as much liquid over as great an area as quickly as possible.

The construction of absorption bodies like that just described is well known to the person skilled in the art and does not need to be described in greater detail. Obviously, the absorption body can contain superabsorbents in the various layers or other added ingredients such as enzyme inhibitors, and substances regulating odour or pH.

FIG. 3a also shows the second leg elastic system 32 which is applied to the absorption body backsheet 41 in conjunction with the first and second absorption layers 42, 43 before the liquid-permeable topsheet 10 is applied. The second leg elastic system is made up of a number of elastic threads which are positioned in a concave shape in order to provide optimum fit and comfort around the legs of the wearer.

The concave or hourglass-shaped form of the whole absorption unit is obtained after the absorption body 12, with its liquid-impermeable backsheet 41 and its liquid-permeable topsheet 10, has been applied to the liquid-impermeable backsheet 11. The material is subsequently cut or punched away so that the leg openings are formed, and the article acquires the characteristic hourglass shape which then forms holes for the legs during use of the article.

In the embodiment shown, the absorption body 12 consists of cellulose fluff with or without the addition of what are known as superabsorbent articles.

However, the absorption body can be made of any material (s) used in absorption bodies for absorbent articles such as diapers, pant diapers, incontinence devices, panty liners or the like. The absorption body 12 can also consist of more than two layers of absorbent material and can also contain a number of layers of liquid-receiving material or the like so as to be capable of rapidly guiding discharged liquid away from the liquid-receiving topsheet 10. Each of the layers comprised by the absorption body 12 can of course contain superabsorbents.

Figure 4:
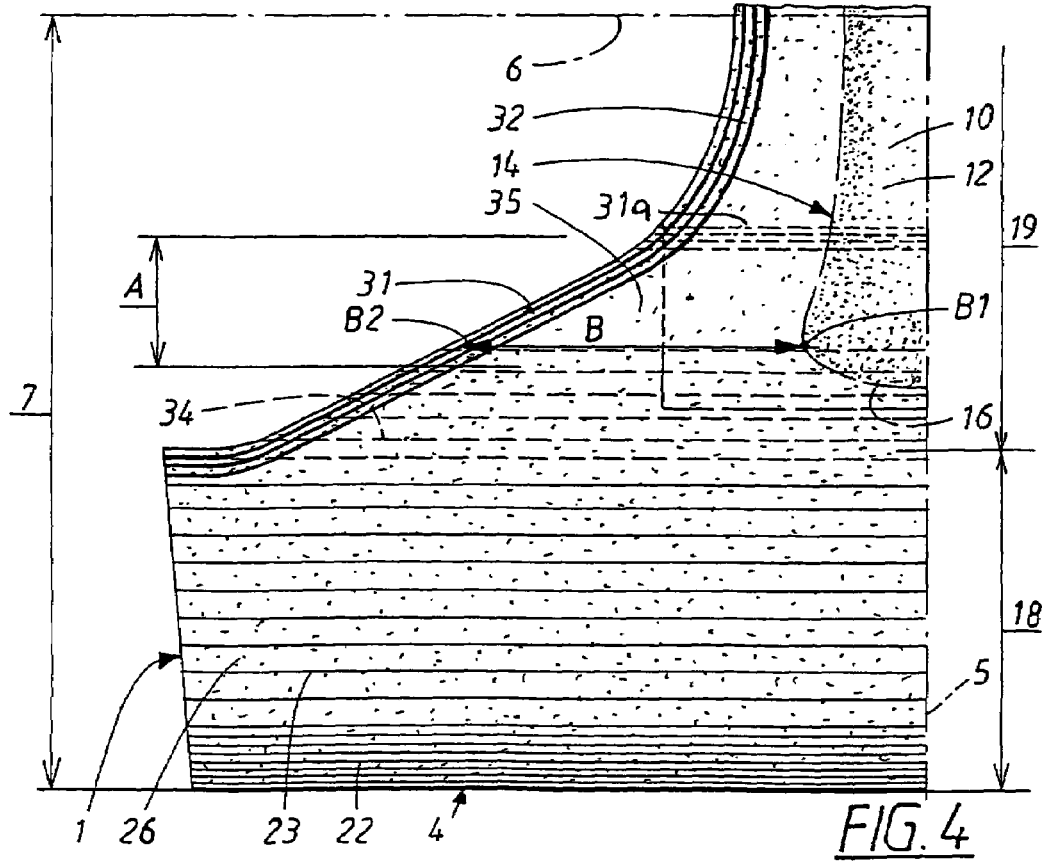
FIG. 4 shows a partial view of the incontinence device in FIGS. 1 and 2.

FIG. 4 shows a part of the article delimited by the longitudinal center line 5 and the transverse center line 6 of the article. The figure also shows a part of one longitudinal side edge 1 and a part of the rear transverse side edge 4, a longitudinal center line 5 and a transverse center line 6. A rear part 7 extending between the transverse center line 6 of the article and the rear transverse side edge 4 of the article is marked in the figure. Also shown is a part of the inner liquid-impermeable topsheet 26, a part of the absorption body 12, with one of its longitudinal side edges 14 and its rear transverse side edge 16, and a part of the liquid-permeable topsheet 10.

The article in its folded-out state in FIG. 4 has a part of the rear end portion 18 located in the rear part 7 of the article, and also the rear part of the crotch portion 19. Also shown are a part of the first rear elastic system 22 and a part of the second rear elastic system 23.

FIG. 4 also shows a part of the first rear leg elastic system 31, a part of the second leg elastic system 32, a part of the third rear elastic system 34 and the pocket 35.

In this embodiment, the distance between the transverse part 31a of the first rear leg elastic system 31, which runs essentially in the same direction as the transverse center line 5 of the article and crosses the crotch portion 19, and the third rear elastic system 34, is roughly 5 cm, and is marked by A in the figure. In the preferred embodiment of the invention, the distance A is generally from about 29 to 81 mm and defines a distance between the rear leg elastic system and the transverse elastic system of the rear portion.

The distance B between a point B1 on the longitudinal side edge 14 of the absorption body 12 located furthest away from the longitudinal center line 5 of the article in the rear part of the crotch portion 19, to a point B2 located in the middle of the first rear leg elastic system 31 on a plane parallel to the transverse center line 6 of the article from the point B1, is roughly 10 cm. The ratio A/B is therefore roughly 0.5.

In another embodiment (not shown), the ratio A/B=0.3-0.7, preferably 0.4-0.6.

What is claimed is:

1. An absorbent article, comprising:
   a liquid-permeable topsheet;
   a liquid-impermeable backsheet;
   an absorption body, having an elongate shape with two longitudinal side edges and two transverse side edges, positioned between the liquid-permeable topsheet and the liquid-impermeable backsheet;
   two longitudinal side edges;
   a longitudinal center line;
   a transverse center line;
   a front end portion;
   a rear end portion;
   a crotch portion lying between the front end and rear end portions, wherein the rear end portion and an adjacent part of the crotch portion have a transverse elastic system;
   a rear leg elastic system including a plurality of elastics extending between the two longitudinal side edges of the article, each of said elastics running continuously along a first leg cutout of the article in the rear part of the crotch portion, crossing the crotch portion essentially parallel to the transverse center line of the article, and along a second leg cutout of the article; and
   a pocket for temporary liquid storage defined laterally outward of the absorption body, on each side thereof, such that said pocket is not disposed on the absorption body, wherein the extent of each of the pockets is limited along an inward side edge of the pocket by the longitudinal side edge of the absorption body, along a rear edge of the pocket by the transverse elastic system, along a forward edge of the pocket by the rear leg elastic system where the rear leg elastic system crosses the crotch portion essentially parallel to the transverse center line of the article and along an outer side edge of the pocket by the rear leg elastic system running along the leg cutout of the article;
   wherein the rear elastic system completely crosses the crotch portion.

2. The absorbent article according to claim 1, wherein the transverse elastic system crosses at least a part of the rear leg elastic system in the rear part of the crotch portion at the leg cutout of the article.

3. The absorbent article according to claim 1, wherein the distance A between the rear leg elastic system and the transverse elastic system, measured along the longitudinal center line of the article, is from 29 to 81 mm.

4. The absorbent article according to claim 1, wherein the transverse elastic system is capable of stretching to 1.8 times the unstretched length of the transverse elastic system.

5. The absorbent article according to claim 1, wherein the transverse elastic system comprises a number of essentially parallel elastic threads with a given mutual spacing.

6. The absorbent article according to claim 1, wherein the transverse elastic system further comprises a second rear elastic system and a third rear elastic system.

7. The absorbent article according to claim 6, wherein the spacing between the elastic threads of the second rear elastic system is smaller than the spacing between the threads in the third rear elastic system.

8. The absorbent article according to claim 1, wherein the absorption body comprises at least a first and a second absorption layer, wherein the first absorption layer is longer in the longitudinal direction than the second absorption layer, and wherein the second absorption layer is at least 16 cm long in the longitudinal direction.

9. The absorbent article according to claim 1, further comprising a front leg elastic system, wherein the distance between the front leg elastic system and the rear leg elastic system in the crotch portion is at least 0.16 cm.

10. An absorbent article, comprising:
    a liquid-permeable topsheet;
    a liquid-impermeable backsheet;
    an absorption body, having an elongate shape with two longitudinal side edges and two transverse side edges, positioned between the liquid-permeable topsheet and the liquid-impermeable backsheet;
    two longitudinal side edges;
    a longitudinal center line;
    a transverse center line;
    a front end portion;
    a rear end portion;
    a crotch portion lying between the front end and rear end portions, wherein the rear end portion and an adjacent part of the crotch portion have a transverse elastic system;
    a rear leg elastic system, comprising a plurality of elastics, each of said elastics running continuously between the two longitudinal side edges of the article along the leg cutout of the article in the rear part of the crotch portion and crossing the crotch portion essentially parallel to the transverse center line of the article to form a crossing portion; and
    a pocket for temporary liquid storage defined laterally outward of the absorption body such that said pocket is not disposed on the absorption body, wherein the extent of each of the pockets is limited by the longitudinal side edge of the absorption body on an inner edge of the pocket, the transverse elastic system at a rear edge of the pocket, the crossing portion of the rear leg elastic system at a front edge of the pocket and the rear leg elastic system along the leg cutout on an outer edge of the pocket;
    wherein the transverse elastic system crosses over at least a part of the rear leg elastic system in the rear part of the crotch portion at the leg cutout of the article;
    wherein the rear leg elastic system completely crosses the crotch portion.

11. The absorbent article according to claim 10, wherein the distance A between the rear leg elastic system and the transverse elastic system, measured along the longitudinal center line of the article, is from 29 to 81 mm.

12. The absorbent article according to claim 10, wherein the transverse elastic system is capable of stretching to 1.8 times the unstretched length of the transverse elastic system.

13. The absorbent article according to claim 10, wherein the transverse elastic system comprises a number of essentially parallel elastic threads with a given mutual spacing.

14. The absorbent article according to claim 10, wherein the transverse elastic system further comprises a second rear elastic system and a third rear elastic system.

15. The absorbent article according to claim 14, wherein the spacing between the elastic threads of the second rear elastic system is smaller than the spacing between the threads in the third rear elastic system.

16. The absorbent article according to claim 10, wherein the absorption body comprises at least a first and a second absorption layer, wherein the first absorption layer is longer in the longitudinal direction than the second absorption layer, and wherein the second absorption layer is at least 16 cm long in the longitudinal direction.

17. The absorbent article according to claim 10, further comprising a front leg elastic system, wherein the distance between the front leg elastic system and the rear leg elastic system in the crotch portion is at least 0.16 cm.

18. An absorbent article, comprising:
a liquid-permeable topsheet;
a liquid-impermeable backsheet;
an absorption body, having an elongate shape with two longitudinal side edges and two transverse side edges, positioned between the liquid-permeable topsheet and the liquid-impermeable backsheet;
two longitudinal side edges;
a longitudinal center line;
a transverse center line;
a front end portion;
a rear end portion;
a crotch portion lying between the front end and rear end portions, wherein the rear end portion and an adjacent part of the crotch portion have a transverse elastic system;
a rear leg elastic system comprising a plurality of elastics, each of said elastics running continuously between the two longitudinal side edges of the article along the leg cutout of the article in the rear part of the crotch portion and crossing the crotch portion essentially parallel to the transverse center line of the article to form a crossing portion; and
a pocket for temporary liquid storage defined laterally outward of the absorption body such that said pocket is not disposed on the absorption body, wherein the extent of each of the pockets is limited by the longitudinal side edge of the absorption body, the transverse elastic system, the rear leg elastic system along the leg cutout and the rear leg elastic system at the crossing portion,
wherein a distance A is defined between the rear leg elastic system crossing the crotch portion essentially parallel to the transverse center line of the article and the transverse elastic system in the crotch portion, a distance B is defined between a first point on the longitudinal side edge of the absorption body located furthest away from the longitudinal center line of the article in the rear part of the crotch portion and a second point located in the middle of the rear leg elastic system running along the leg cutout of the article in the rear part of the crotch portion on a plane parallel to the transverse center line of the article from the first point, and the ratio of A/B is approximately 0.3-0.7;
wherein the rear leg elastic system completely crosses the crotch portion.

19. An absorbent article, comprising:
a liquid-permeable topsheet;
a liquid-impermeable backsheet;
an absorption body, having an elongate shape with two longitudinal side edges and two transverse side edges, positioned between the liquid-permeable topsheet and the liquid-impermeable backsheet;
two longitudinal side edges;
a longitudinal center line;
a transverse center line;
a front end portion;
a rear end portion;
a crotch portion lying between the front end and rear end portions, wherein the rear end portion and an adjacent part of the crotch portion have a transverse elastic system;
a rear leg elastic system including a plurality of elastics extending between the two longitudinal side edges of the article, each of said elastics running continuously along a first leg cutout of the article in the rear part of the crotch portion, crossing the crotch portion essentially parallel to the transverse center line of the article, and along a second leg cutout of the article; and
a pocket for temporary liquid storage defined laterally outward of the absorption body, on each side thereof, such that said pocket is not disposed on the absorption body, wherein the extent of each of the pockets is limited along an inward side edge of the pocket by the longitudinal side edge of the absorption body, along a rear edge of the pocket by the transverse elastic system, along a forward edge of the pocket by the rear leg elastic system where the rear leg elastic system crosses the crotch portion essentially parallel to the transverse center line of the article and along an outer side edge of the pocket by the rear leg elastic system running along the leg cutout of the article;
wherein the absorption body at least partially overlaps the transverse elastic system.

20. An absorbent article, comprising:
a liquid-permeable topsheet;
a liquid-impermeable backsheet;
an absorption body, having an elongate shape with two longitudinal side edges and two transverse side edges, positioned between the liquid-permeable topsheet and the liquid-impermeable backsheet;
two longitudinal side edges;
a longitudinal center line;
a transverse center line;
a front end portion;
a rear end portion;
a crotch portion lying between the front end and rear end portions, wherein the rear end portion and an adjacent part of the crotch portion have a transverse elastic system;
a rear leg elastic system, comprising a plurality of elastics, each of said elastics running continuously between the two longitudinal side edges of the article along the leg cutout of the article in the rear part of the crotch portion and crossing the crotch portion essentially parallel to the transverse center line of the article to form a crossing portion; and
a pocket for temporary liquid storage defined laterally outward of the absorption body such that said pocket is not disposed on the absorption body, wherein the extent of each of the pockets is limited by the longitudinal side edge of the absorption body on an inner edge of the pocket, the transverse elastic system at a rear edge of the pocket, the crossing portion of the rear leg elastic system at a front edge of the pocket and the rear leg elastic system along the leg cutout on an outer edge of the pocket;
wherein the transverse elastic system crosses over at least a part of the rear leg elastic system in the rear part of the crotch portion at the leg cutout of the article;

wherein the absorption body at least partially overlaps the transverse elastic system.

21. An absorbent article, comprising:
a liquid-permeable topsheet;
a liquid-impermeable backsheet;
an absorption body, having an elongate shape with two longitudinal side edges and two transverse side edges, positioned between the liquid-permeable topsheet and the liquid-impermeable backsheet;
two longitudinal side edges;
a longitudinal center line;
a transverse center line;
a front end portion;
a rear end portion;
a crotch portion lying between the front end and rear end portions, wherein the rear end portion and an adjacent part of the crotch portion have a transverse elastic system;
a rear leg elastic system comprising a plurality of elastics, each of said elastics running continuously between the two longitudinal side edges of the article along the leg cutout of the article in the rear part of the crotch portion and crossing the crotch portion essentially parallel to the transverse center line of the article to form a crossing portion; and a pocket for temporary liquid storage defined laterally outward of the absorption body such that said pocket is not disposed on the absorption body, wherein the extent of each of the pockets is limited by the longitudinal side edge of the absorption body, the transverse elastic system, the rear leg elastic system along the leg cutout and the rear leg elastic system at the crossing portion, wherein a distance A is defined between the rear leg elastic system crossing the crotch portion essentially parallel to the transverse center line of the article and the transverse elastic system in the crotch portion, a distance B is defined between a first point on the longitudinal side edge of the absorption body located furthest away from the longitudinal center line of the article in the rear part of the crotch portion and a second point located in the middle of the rear leg elastic system running along the leg cutout of the article in the rear part of the crotch portion on a plane parallel to the transverse center line of the article from the first point, and the ratio of A/B is approximately 0.3-0.7;

wherein the absorption body at least partially overlaps the transverse elastic system.

\* \* \* \* \*